United States Patent
Jung et al.

(10) Patent No.: US 12,055,487 B2
(45) Date of Patent: Aug. 6, 2024

(54) APPARATUS AND METHOD FOR ANALYZING SUBSTANCE OF OBJECT

(71) Applicant: SAMSUNG ELECTRONICS CO., LTD., Suwon-si (KR)

(72) Inventors: Myoung Hoon Jung, Bucheon-si (KR); Sang Kyu Kim, Yongin-si (KR); Yoon Jae Kim, Seoul (KR); Hyun Seok Moon, Hwaseong-si (KR); Jin Young Park, Hwaseong-si (KR); Sung Mo Ahn, Yongin-si (KR); Kun Sun Eom, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 267 days.

(21) Appl. No.: 17/077,700

(22) Filed: Oct. 22, 2020

(65) Prior Publication Data
US 2021/0404953 A1    Dec. 30, 2021

(30) Foreign Application Priority Data

Jun. 25, 2020    (KR) .................. 10-2020-0077783

(51) Int. Cl.
*G01N 21/47*    (2006.01)
*A61B 5/00*    (2006.01)
(Continued)

(52) U.S. Cl.
CPC ....... *G01N 21/47* (2013.01); *H01L 27/14621* (2013.01); *H01L 27/14643* (2013.01); *A61B 5/681* (2013.01); *G01N 21/65* (2013.01)

(58) Field of Classification Search
None
See application file for complete search history.

(56) References Cited

U.S. PATENT DOCUMENTS 5,771,094 A * 6/1998 Carter ................. G01J 4/00
                                                356/369
8,355,545 B2 * 1/2013 Corcoran ............ G06V 10/56
                                                382/124
(Continued)

FOREIGN PATENT DOCUMENTS

JP    2016-186421 A    10/2016
JP    2016186421 A  * 10/2016
(Continued)

OTHER PUBLICATIONS

Communication dated Jun. 14, 2021, issued by the European Patent Office in counterpart European Application No. 20217555.0.
(Continued)

*Primary Examiner* — Tarifur R Chowdhury
*Assistant Examiner* — Roberto Fabian, Jr.
(74) *Attorney, Agent, or Firm* — Sughrue Mion, PLLC

(57) ABSTRACT

An apparatus for analyzing a substance of an object in a non-invasive manner is provided. The apparatus for analyzing a substance of an object includes: a sensor part including an image sensor, and a plurality of light sources disposed around the image sensor; and a processor configured to drive the plurality of light sources to obtain absorbance of each pixel of the image sensor based on an intensity of light received by each pixel, to correct the absorbance of each pixel based on a distance between the plurality of light sources and each pixel, and to analyze a substance of an object based on the corrected absorbance of each pixel.

25 Claims, 16 Drawing Sheets

(51) Int. Cl.
  *G01N 21/65* (2006.01)
  *H01L 27/146* (2006.01)

(56) References Cited

U.S. PATENT DOCUMENTS

| | | | |
|---|---|---|---|
| 9,186,112 B2 | 11/2015 | Bechtel et al. | |
| 9,216,000 B2 | 12/2015 | Bechtel et al. | |
| 9,345,439 B2 | 5/2016 | Bechtel et al. | |
| 9,392,978 B2 | 7/2016 | Bechtel et al. | |
| 9,398,870 B2 | 7/2016 | Bechtel et al. | |
| 9,498,157 B2 | 11/2016 | Bechtel et al. | |
| 9,888,872 B2 | 2/2018 | Bechtel et al. | |
| 10,213,142 B2 | 2/2019 | Bechtel et al. | |
| 10,234,445 B2 * | 3/2019 | Ghosh | G01N 21/6452 |
| 10,278,592 B2 | 5/2019 | Fish et al. | |
| 10,335,069 B2 | 7/2019 | Bechtel et al. | |
| 10,390,705 B2 | 8/2019 | Ou-Yang et al. | |
| 10,416,079 B2 | 9/2019 | Magnussen et al. | |
| 10,433,739 B2 | 10/2019 | Weekly et al. | |
| 10,456,066 B2 | 10/2019 | Bechtel et al. | |
| 10,466,783 B2 | 11/2019 | Newberry | |
| 10,492,715 B2 | 12/2019 | Bechtel et al. | |
| 10,524,705 B2 | 1/2020 | Bechtel et al. | |
| 10,638,961 B2 * | 5/2020 | Al-Ali | A61B 5/14546 |
| 10,682,080 B2 | 6/2020 | Bechtel et al. | |
| 10,713,458 B2 | 7/2020 | Bhat et al. | |
| 10,912,503 B2 | 2/2021 | Bechtel et al. | |
| 10,931,859 B2 | 2/2021 | Bhat et al. | |
| 10,939,853 B2 | 3/2021 | Bechtel et al. | |
| 2002/0058865 A1 * | 5/2002 | Cheng | A61B 5/14551 600/323 |
| 2002/0106051 A1 * | 8/2002 | Menhardt | G01N 23/04 378/4 |
| 2004/0259187 A1 | 12/2004 | Aldini et al. | |
| 2006/0134004 A1 | 6/2006 | Gellermann et al. | |
| 2008/0081968 A1 * | 4/2008 | Numada | A61B 5/02007 606/2 |
| 2010/0290051 A1 * | 11/2010 | Yamada | G01N 21/8483 356/445 |
| 2011/0051125 A1 * | 3/2011 | Kim | A61B 5/6887 356/440 |
| 2013/0289414 A1 * | 10/2013 | Adibnazari | A61B 5/443 600/476 |
| 2013/0317331 A1 | 11/2013 | Bechtel et al. | |
| 2013/0324816 A1 | 12/2013 | Bechtel et al. | |
| 2014/0046152 A1 | 2/2014 | Bechtel et al. | |
| 2014/0148661 A1 | 5/2014 | Bechtel et al. | |
| 2014/0148662 A1 | 5/2014 | Bechtel et al. | |
| 2014/0155716 A1 | 6/2014 | Bechtel et al. | |
| 2014/0339428 A1 * | 11/2014 | O'Brien | A61J 7/04 368/10 |
| 2015/0254495 A1 * | 9/2015 | Rowe | A61B 5/0059 382/124 |
| 2016/0073942 A1 | 3/2016 | Bechtel et al. | |
| 2016/0100781 A1 | 4/2016 | Bechtel et al. | |
| 2016/0262665 A1 | 9/2016 | Bechtel et al. | |
| 2016/0324453 A1 | 11/2016 | Bechtel et al. | |
| 2016/0331288 A1 | 11/2016 | Bechtel et al. | |
| 2017/0071517 A1 | 3/2017 | Bechtel et al. | |
| 2017/0343476 A1 * | 11/2017 | Boege | G02B 21/10 |
| 2018/0092580 A1 | 4/2018 | Bechtel et al. | |
| 2018/0168493 A1 | 6/2018 | Bechtel et al. | |
| 2018/0168494 A1 | 6/2018 | Bechtel et al. | |
| 2018/0368693 A1 * | 12/2018 | Secco | A61B 5/0082 |
| 2019/0008431 A1 | 1/2019 | Bechtel et al. | |
| 2019/0150746 A1 | 5/2019 | Kim | |
| 2019/0167199 A1 | 6/2019 | Nam et al. | |
| 2019/0175084 A1 | 6/2019 | Bechtel et al. | |
| 2019/0277764 A1 | 9/2019 | Chang et al. | |
| 2019/0320958 A1 | 10/2019 | Bechtel et al. | |
| 2020/0029873 A1 | 1/2020 | Park et al. | |
| 2020/0060588 A1 | 2/2020 | Bechtel et al. | |
| 2020/0107761 A1 | 4/2020 | Bechtel et al. | |
| 2020/0138348 A1 | 5/2020 | Bechtel et al. | |
| 2020/0305775 A1 | 10/2020 | Bechtel et al. | |
| 2020/0342194 A1 | 10/2020 | Bhat et al. | |
| 2021/0161443 A1 | 6/2021 | Bechtel et al. | |

FOREIGN PATENT DOCUMENTS

| | | |
|---|---|---|
| KR | 10-2015-0005700 A | 1/2015 |
| WO | 2017/214582 A1 | 12/2017 |

OTHER PUBLICATIONS

Kim et al., "RGBD Camera based Material Recognition via Surface Roughness Estimation," 2018 IEEE Winter Conference on Applications of Computer Vision, Total 9 pages.

* cited by examiner

APPARATUS AND METHOD FOR ANALYZING SUBSTANCE OF OBJECT

CROSS-REFERENCE TO RELATED APPLICATION(S)

This application claims priority from Korean Patent Application No. 10-2020-0077783, filed on Jun. 25, 2020, in the Korean Intellectual Property Office, the entire disclosure of which is herein incorporated by reference for all purposes.

BACKGROUND

1. Field

Embodiments of the disclosure relate to an apparatus and a method for analyzing a substance of an object using a complementary metal-oxide semiconductor (CMOS) image sensor.

2. Description of the Related Art

An antioxidant plays an important role in removing free radicals, which are harmful to a human body, thereby protecting skin from aging, and maintaining human health. A typical example of an antioxidant is carotenoid, and there has been research to measure carotenoid in a non-invasive manner. A Raman measurement method and an absorbance-based measurement method are generally used to measure an antioxidant signal. The Raman measurement method may have high measurement accuracy but has drawbacks in that the equipment is expensive and is difficult to be manufactured in a compact size. Recently, research is actively underway on reflective absorbance-based measurement methods to be applied to various devices such as wearable devices and the like.

The antioxidant measurement method based on absorbance measurement generally includes the following two methods. A first method is to use a white light as a light source, and use a photo diode (PD) as a detector for receiving light having specific wavelengths of, for example, 480 nm, 610 nm, etc., by passing the light through a band pass filter (BPF). However, this method may be significantly affected by a change in hemoglobin signals due to pressure. A second method is to use multi-wavelength light emitting diodes (LEDs) (e.g., wavelengths of red, green, blue, and white) and a photo diode. However, this method has drawbacks in that the manufacturing process is complicated and requires high production cost.

SUMMARY

According to an aspect of an example embodiment, provided is an apparatus for analyzing a substance of an object, the apparatus including: a sensor part including an image sensor and a plurality of light sources, the plurality of light sources being disposed around the image sensor; and a processor configured to drive the plurality of light sources to obtain absorbance of each pixel of the image sensor based on an intensity of light received by each pixel, configured to correct the absorbance of each pixel based on a distance between the plurality of light sources and each pixel, and configured to analyze a substance of an object based on the corrected absorbance of each pixel.

The image sensor may include a complementary metal-oxide semiconductor (CMOS) image sensor.

The plurality of light sources may be disposed evenly around the image sensor.

A first portion of the plurality of light sources may be disposed on a first side of the image sensor, and a second portion of the plurality of light sources may be disposed on a second side, the second side facing the first side.

The plurality of light sources may include light sources configured to emit light of different wavelengths.

The image sensor may include a color filter configured to adjust a measurement wavelength band.

Light sources configured to emit light of a same wavelength, among the plurality of light sources, may be disposed to face each other.

The plurality of light sources may be configured to emit light of a single wavelength, and the image sensor may include a color filter configured to adjust a measurement wavelength band.

The processor may be further configured to sequentially drive each of the plurality of light sources in a predetermined direction or in a unit of a predetermined wavelength.

The processor maybe further configured to, based on at least one of a measurement position or a measurement depth, select light sources among the plurality of light sources, and sequentially drive the selected light sources in a predetermined direction or in a unit of a predetermined wavelength.

The processor may be further configured to combine the corrected absorbance of each pixel for each of the plurality of light sources, and analyze the substance of the object based on a result of combination.

The processor maybe further configured to, based on the absorbance of each pixel of the image sensor, analyze the substance for each pixel position of the object.

The processor may be further configured to correct the absorbance of each pixel by using a square of the distance between the plurality of light sources and each pixel of the image sensor, or a logarithmic function.

The processor may be further configured to exclude a light source, which does not satisfy a predetermined criterion, based on the absorbance of each pixel with respect to each of the plurality of light sources, and analyze the substance of the object based on the absorbance of each pixel with respect to remaining light sources, excluding the light source.

The substance of the object may include at least one of carotenoid, triglyceride, blood glucose, calories, cholesterol, protein, uric acid, water, or chromophore.

According to an aspect of an example embodiment, provided is an apparatus for analyzing a substance of an object, the apparatus including: a sensor part including an image sensor, a plurality of first light sources disposed around the image sensor, and a second light source for fingerprint recognition; and a processor configured to drive the second light source to perform user authentication based on a fingerprint image of a finger obtained by the image sensor, and based on a successful user authentication, configured to drive the plurality of first light sources to obtain absorbance of each pixel of the image sensor based on an intensity of light received by each pixel, configured to correct the absorbance of each pixel based on a distance between the plurality of first light sources and each pixel, and configured to analyze a substance of an object based on the corrected absorbance of each pixel.

The apparatus may further include a storage configured to store a light source driving condition corresponding to each user, and the processor may be further configured to, based on the successful user authentication, drive the plurality of first light sources based on a light source driving condition corresponding to an authenticated user.

The apparatus may further include a storage configured to store a substance analysis history of each user, and the processor may be further configured to, based on completion of analysis of the substance of the object, update a substance analysis history of an authenticated user.

The processor may be further configured to provide information related to a contact position of the finger based on the fingerprint image.

The processor may be further configured to detect a position of a characteristic point of the finger based on the fingerprint image, and provide the information based on a distance between the detected characteristic point and a center of the image sensor.

The processor may be further configured to detect a position of a characteristic point of the finger based on the fingerprint image, determine a pixel of interest among pixels of the image sensor, and obtain the absorbance based on an intensity of light at the determined pixel of interest.

The processor may be further configured to detect a position of a characteristic point of the finger based on the fingerprint image, and determine light sources to be driven among the plurality of first light sources based on the detected position of the characteristic point.

According to an aspect of an example embodiment, provided is a method of analyzing a substance of an object, the method including: emitting light onto an object by driving a plurality of light sources disposed around an image sensor; receiving light, scattered or reflected from the object, through the image sensor; obtaining absorbance of each pixel of the image sensor based on an intensity of light received by each pixel; correcting the absorbance of each pixel based on a distance between the plurality of light sources and each pixel; and analyzing a substance of an object based on the corrected absorbance of each pixel.

The emitting may include sequentially driving each of the plurality of light sources in a predetermined direction or in a unit of a predetermined wavelength.

The emitting may include, based on at least one of a measurement position or a measurement depth, selecting light sources among the plurality of light sources, and sequentially driving the selected light sources in the predetermined direction or in the unit of the predetermined wavelength.

The analyzing may include combining the corrected absorbance of each pixel for each of the plurality of light sources, and analyzing the substance of the object based on a result of the combining.

The analyzing may include, based on the absorbance of each pixel, analyzing the substance for each pixel position of the object.

The correcting may include, by using a square of the distance between the plurality of light sources and each pixel of the image sensor, or a logarithmic function, correcting the absorbance of each pixel for the plurality of light sources.

BRIEF DESCRIPTION OF THE DRAWINGS

The above and other aspects, features, and advantages of certain embodiments of the disclosure will be more apparent from the following description taken in conjunction with the accompanying drawings.

DETAILED DESCRIPTION

Figure 1:
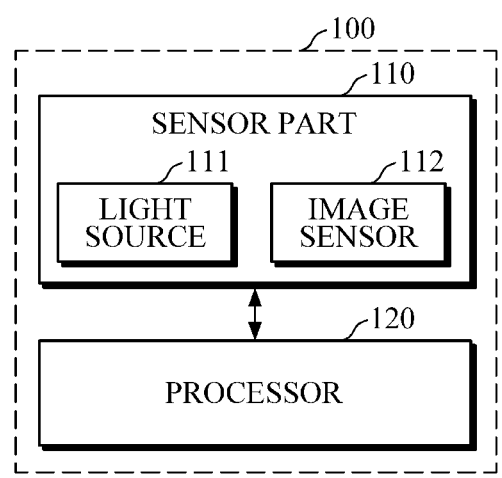
FIG. 1 is a block diagram illustrating an apparatus for analyzing a substance according to an embodiment of the disclosure.

Details of example embodiments are included in the following detailed description and drawings. Advantages and features of the disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Hereinafter, example embodiments of an apparatus and a method for analyzing a substance of an object will be described in detail with reference to the accompanying drawings.

FIG. 1 is a block diagram illustrating an apparatus 100 for analyzing a substance according to an embodiment of the disclosure. FIGS. 2A to 2D are diagrams illustrating examples of a structure of a sensor part in the apparatus 100. FIGS. 3A and 3B are diagrams illustrating examples of driving light sources of a sensor part in the apparatus 100. FIG. 3C is a diagram illustrating an example of a general relationship between a carotenoid concentration and light absorbance.

Referring to FIG. 1, the apparatus 100 for analyzing a substance includes a sensor part 110 and a processor 120.

The sensor part 110 may include a plurality of light sources 111 and an image sensor 112. The plurality of light sources may include a light emitting diode (LED), a laser diode (LD), a phosphor, and the like. All of the plurality of light sources 111 may emit light of the same single wavelength or light of different wavelengths. In this case, the different wavelengths may include an infrared wavelength, a red wavelength, a green wavelength, a blue wavelength, a white wavelength, and the like. Alternatively, the plurality of light sources 111 may emit light of two different wavelengths, in which case a number of light sources 111 may be determined to be a multiple of a minimum required number of wavelengths. For example, in order to emit light of three different wavelengths, at least two light sources may be provided for each wavelength.

The image sensor 112 may be a complementary metal-oxide semiconductor (CMOS) image sensor. However, the image sensor 112 is not limited thereto, and may be a charge-coupled device (CCD) image sensor. Further, instead of the image sensor 112, for example, an array of photodiodes may be formed. In an example embodiment, a multi-wavelength sensor part having multiple optical paths may be provided in a compact size by using, for example, LEDs and the CMOS image sensor having high spatial resolution.

The sensor part 110 may have various shapes, such as a fan shape, a circular shape, an oval shape, a polygonal shape, etc., according to a shape of a form factor. For example, the sensor part 110 may be formed in a circular shape, an oval shape, a square shape, etc., with the image sensor 112 being disposed at the center thereof, and the plurality of light sources 111 being disposed evenly around the periphery of the image sensor 112. In another example, the sensor part 110 may be formed in a circular shape, an oval shape, a square shape, etc., with the image sensor 112 being disposed at the center thereof, and the plurality of light sources 111 being disposed at a first side of image sensor 112 and a second side of the image sensor facing the first side. However, the shape of the sensor part 110 and the arrangement of the image sensor 112 and the plurality of light sources 111 are not limited to the above examples.

Figure 2A:
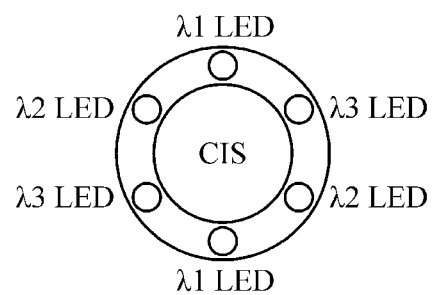
FIGS. 2A to 2D are diagrams illustrating examples of a structure of a sensor part in an apparatus for analyzing a substance according to an embodiment of the disclosure.
Figure 3A:
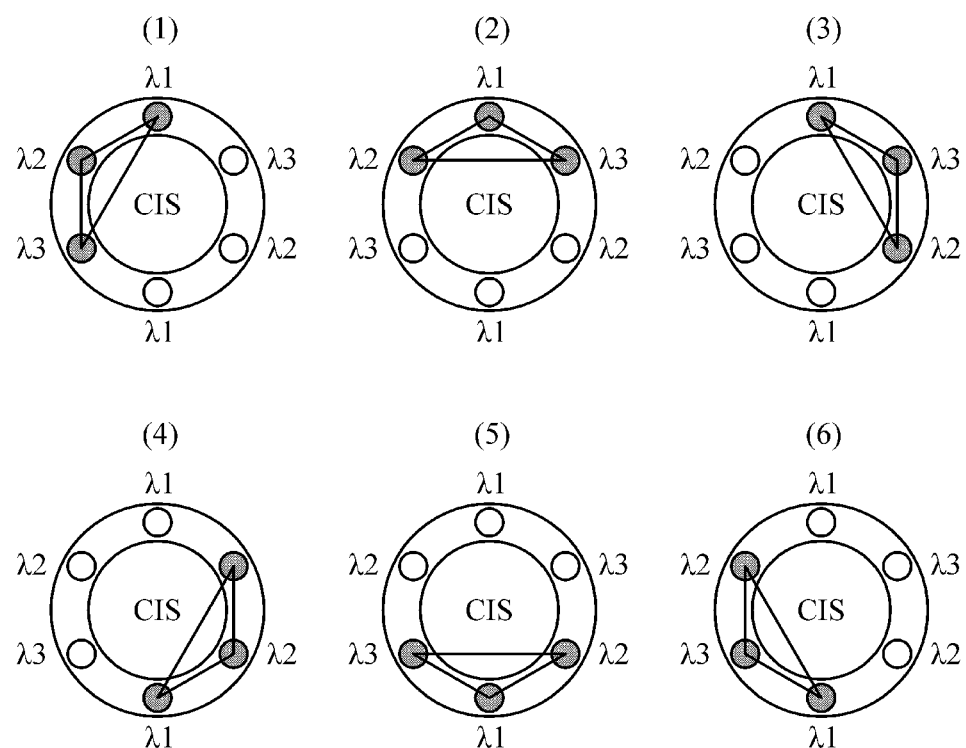
FIGS. 3A and 3B are diagrams illustrating examples of driving light sources of a sensor part in an apparatus for analyzing a substance according to an embodiment of the disclosure.
Figure 3B:
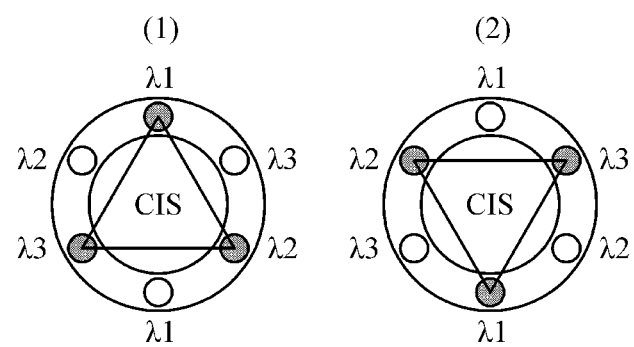
Figure 3C:
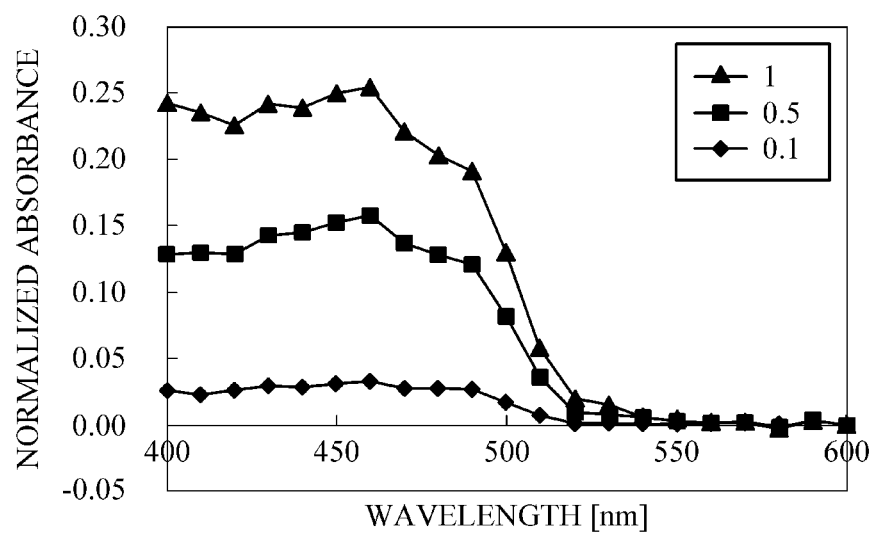
FIG. 3C is a diagram illustrating an example of a general relationship between a carotenoid concentration and absorbance.

Referring to FIG. 2A, the sensor part 110 is formed in a circular shape, with the CMOS image sensor (CIS) being disposed at the center thereof, and six LEDs being disposed evenly around the periphery of the CIS. The six LEDs, including three pairs, may emit light of three different wavelengths $\lambda 1$, $\lambda 2$ and $\lambda 3$, and may be disposed to face each other diagonally with respect to the CIS. However, the number of LEDs, the number of wavelengths, and the number of LEDs for each wavelength, and the like are not particularly limited thereto.

Figure 2B:
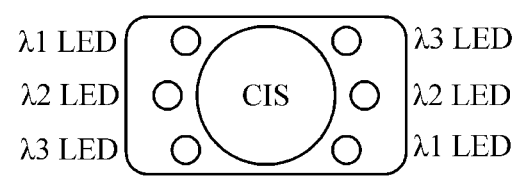

Referring to FIG. 2B, the sensor part 110 is formed in a rectangular shape, with the CMOS image sensor (CIS) being disposed at the center thereof, and six LEDs being disposed on both sides of the CIS. In this case, the LEDs may be disposed on both sides of the CIS to emit three different wavelengths $\lambda 1$, $\lambda 2$ and $\lambda 3$, as illustrated in FIG. 2B.

Figure 2C:
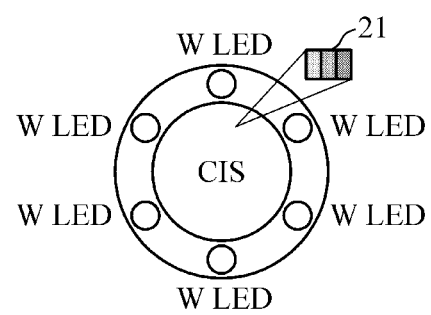
Figure 2D:
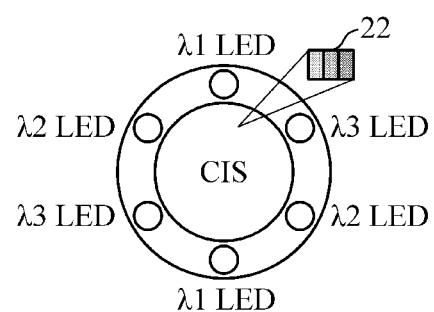

Referring to FIG. 2C, all the plurality of LEDs of the sensor part 110 may emit light of the same single wavelength, e.g., white wavelength. In this case, the CIS, including a color filter 21 for adjusting a measurement wavelength band, may obtain information for each wavelength. Referring to FIG. 2D, some of the plurality of LEDs of the sensor part 110 may emit light of different wavelengths, and the sensor part 110 may include a color filter 22 for adjusting a measurement wavelength band in the CIS. As illustrated in FIG. 2D, while increasing a signal strength of a specific wavelength by using the multi-wavelength LEDs, a measurement wavelength band may be precisely adjusted by using the color filter 22 of the CIS.

Referring back to FIG. 1, the processor 120 may be electrically connected to the sensor part 110. In response to a request for analyzing a substance of an object, the processor 120 may drive the plurality of light sources 111 of the sensor part 110, and may analyze the substance of the object based on data measured by the image sensor 112. In this case, the substance of the object may include carotenoid, triglyceride, blood glucose, calories, cholesterol, protein, uric acid, water, chromophore, and the like.

For example, the processor 120 may sequentially drive all of the plurality of light sources in a time-division manner in a pre-defined direction, such as a clockwise or counterclockwise direction or a zigzag direction. Alternatively, the processor 120 may drive the light sources in the order of short to long wavelengths, or vice versa. For example, referring to FIG. 2A, the processor 120 may first turn on LEDs of the first wavelength $\lambda 1$ at the same time and turn off the remaining LEDs of other wavelengths. After a lapse of a predetermined period of time, the processor 120 may turn on LEDs of the second wavelength $\lambda 2$ at the same time and turn off the remaining LEDs of other wavelengths. After a lapse of a predetermined period of time, the processor 120 may turn on LEDs of the third wavelength $\lambda 3$ at the same time and turn off the remaining LEDs of other wavelengths. In this case, driving conditions of the light sources, e.g., a driving sequence and a current strength of light sources, a pulse duration, etc., may be pre-defined.

In another example, the processor 120 may select some of the plurality of light sources 111 according to a measurement position, measurement depth, etc., and may sequentially drive the selected light sources 111 in a predetermined direction or in a predetermined order of wavelength.

Referring to FIG. 3A, in order to analyze a substance in an outer region of an object or at a shallow depth in the object that is in contact with the sensor part 110, CIS data may be obtained in six outer regions by combining adjacent light sources of three wavelengths $\lambda 1$, $\lambda 2$, $\lambda 3$, and a substance in the outer regions or at the shallow depth may be analyzed by using six combinations of the obtained CIS data. In this case, the CIS data may indicate intensities of light received by each pixel of the CIS. Referring to FIG. 3B, in order to analyze a substance in a central region of an object or at a deep depth in the object that is in contact with the sensor part 110, CIS data may be obtained by combining light sources of three different wavelengths which are disposed at a longest distance from each other, and a substance in the central region or at the deep depth may be analyzed by using two combinations of the obtained CIS data. However, these are merely examples, and various other combinations may also be provided. In this manner, signals in various optical paths may be obtained even by a small-sized sensor part, and may be used to analyze a substance for each depth.

By driving the plurality of light sources 111, the processor 120 may analyze a substance of an object based on pixel data received by the image sensor 112, i.e., based on intensities of light received by each pixel of the image sensor 112. For example, the processor 120 may calculate light absorbance of each pixel by using the light intensity of each pixel based on light received by the image sensor 112, and may analyze a substance based on the absorbance of each pixel. FIG. 3C illustrates a relationship between absorbance and a carotenoid concentration, showing that there is a constant correlation between the absorbance and the carotenoid concentration in a predetermined wavelength band. The absorbance may be obtained by using the following Equation 1, which is an equation for calculating absorbance based on the Lambert-Beer's law.

$$A = \log_{10} \frac{I_0}{I} = \varepsilon bc \qquad \text{[Equation 1]}$$

Herein, A denotes the absorbance, $I_0$ denotes a measured intensity of incident light, which is measured by using a standard reflector, and I denotes the intensity of light reflected from the object, i.e., the intensity of light received by each pixel of the image sensor 112. Further, c denotes a pre-defined absorption coefficient, b denotes an optical path, and c denotes a substance concentration.

Upon obtaining the absorbance of each pixel for a specific light source 111, the processor 120 may correct the absorbance of each pixel to minimize an effect of a distance between the light source 111 and each pixel. For example, the processor 120 may correct the absorbance of each pixel based on the distance between the light source 111 and each pixel of the image sensor 112. The following Equation 2 is an example of correcting the absorbance of each pixel.

$$A' = A/f(d) \qquad \text{[Equation 2]}$$

Herein, A denotes the absorbance of each pixel, and A' denotes the corrected absorbance of each pixel. Further, d denotes the distance between the driven light source and each pixel of the image sensor 112; and f(d) denotes a pre-defined function for the distance (d), e.g., a function of the square of the distance or a logarithmic function, but is not limited thereto.

Upon correcting the absorbance of each pixel for each of the plurality of light sources 111, the processor 120 may analyze a substance of the object by properly combining the absorbance values of each pixel for each of the light sources 111.

For example, by using absorbance of each pixel for a first light source and absorbance of each pixel for a second light source, the processor 120 may combine absorbance values of corresponding pixels based on a statistical value, such as a mean value, a median value, etc., or using a pre-defined function, and may estimate a carotenoid concentration at each position of the object, which corresponds to each pixel, based on the combined absorbance values of each pixel using the above Equation 1. In this case, the first light source and the second light source do not mean two light sources, but are used only to distinguish each of the driven light sources from each other.

In another example, the processor 120 may estimate a first carotenoid concentration at each position of the object based on the absorbance of each pixel for the first light source, and may estimate a second carotenoid concentration at each position of the object based on the absorbance of each pixel for the second light source. In this case, if a wavelength of the first light source is different from a wavelength of the second light source, the processor 120 may analyze a carotenoid substance at different measurement depths and positions of the object.

Alternatively, the processor 120 may calculate one absorbance value for each light source by, for example, averaging the absorbance values of each pixel for each of the light sources, and based on the calculated one absorbance value, the processor 120 may analyze, for each pixel, the carotenoid concentration of all the regions that are in contact with the sensor part 110. Alternatively, as described above, the processor 120 may estimate the carotenoid concentration of the region, being in contact with the sensor part 110, by combining all the absorbance values of each pixel for all the driven light sources. However, the processor 120 is not limited to these examples, and may analyze a substance by using various methods according to a measurement depth, a measurement position, a measurement purpose, and the like.

Furthermore, the processor 120 may exclude a light source, which does not satisfy a predetermined criterion, based on the light intensity or absorbance of each pixel for each of the light sources, and may analyze a substance based on the absorbance of each pixel for the remaining light sources. For example, the processor 120 may obtain a statistical value, such as a mean value, a median value, etc., of the light intensities or absorbances of each pixel for each of the light sources, and may exclude a light source having the obtained statistical value which is outside of a predetermined range. Alternatively, the processor 120 may exclude a light source having a highest or lowest statistical value of the absorbances of each pixel obtained for each of the light sources. However, these are merely examples.

Figure 4:
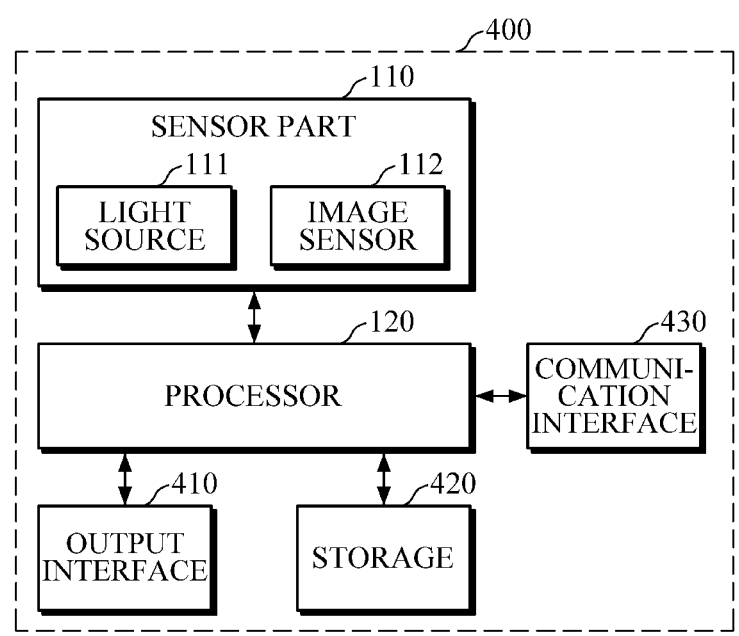
FIG. 4 is a block diagram illustrating an apparatus for analyzing a substance according to another embodiment of the disclosure.

FIG. 4 is a block diagram illustrating an apparatus 400 for analyzing a substance according to another embodiment of the disclosure.

Referring to FIG. 4, the apparatus 400 for analyzing a substance includes the sensor part 110, the processor 120, an output interface 410, a storage 420, and a communication interface 430. The sensor part 110 includes the light source 111 and the image sensor 112. The sensor part 110 and the processor 120 are described above in detail.

The output interface 410 may provide a processing result of the processor 120 to a user. For example, the output interface 410 may display a processing result of the processor 120 on a display. The output interface 410 may divide a display area into two or more areas, and may output information related to absorbance, which is used for analyzing a substance, in a first area and a substance analysis result in a second area. Further, the output interface 410 may output data showing a substance analysis history over a predetermined period of time in the form of graphs in the first area; and when a user selects an analysis result at any one point in time in a graph, the output interface 410 may output a substance analysis result at the selected time in the second area. In this case, if an estimated substance value falls outside a normal range, the output interface 410 may provide warning information by changing color, line thickness, etc., or displaying the abnormal value along with a normal range, so that the user may easily recognize the abnormal value of the estimated substance value of the user. Further, either along with the visual output or alone, the output interface 410 may output the substance analysis result using a non-visual method by voice, vibrations, tactile sensation, and the like through a voice output module such as a speaker, a haptic module, and the like.

The storage 420 may store reference information to be used for substance analysis, results processed by the sensor part 110 and/or the processor 120, e.g., data showing intensities of light from each light source received at each pixel, absorbance of each pixel, corrected absorbance of each pixel, a substance analysis result, and the like. The reference information may include user characteristic information such as a user's age, gender, health condition, and the like. In addition, the reference information may include light source driving conditions, a substance analysis model, and the like.

The storage 420 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 430 may communicate with an external device to transmit and receive various data, related to substance analysis, to and from the external device. In this case, the external device may include an information processing device such as a smartphone, a tablet PC, a desktop computer, a laptop computer, and the like. For example, the communication interface 430 may transmit a substance analysis result to a user's smartphone and the like, so that the user may manage and monitor the substance analysis result (e.g., by using a device having a relatively high performance). However, the communication interface 430 is not limited thereto.

The communication interface 430 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are merely examples and are not intended to be limiting.

Figure 5:
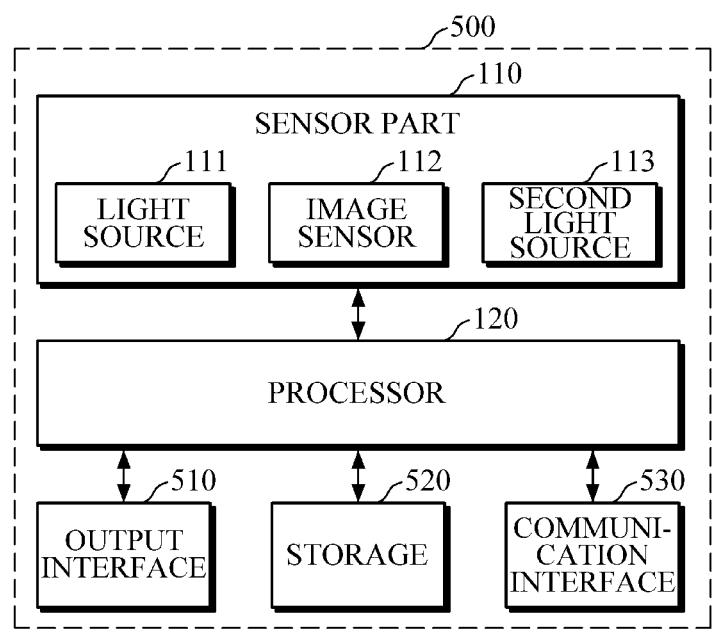
FIG. 5 is a block diagram illustrating an apparatus for analyzing a substance according to yet another embodiment of the disclosure.
Figure 6:
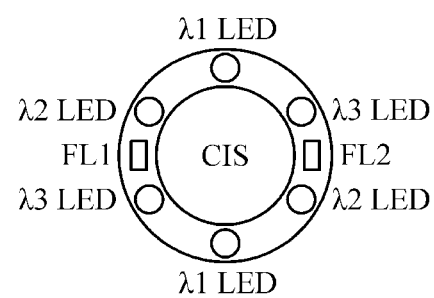
FIG. 6 is a diagram illustrating an example of a structure of a sensor part of FIG. 5.
Figure 7A:
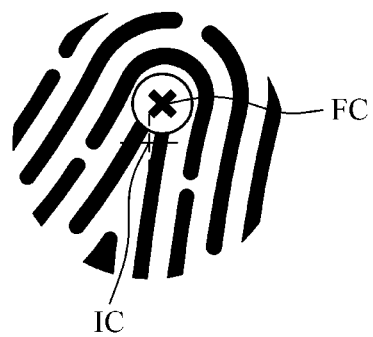
FIGS. 7A and 7B are diagrams illustrating an example of guiding a contact position based on a fingerprint image according to an embodiment of the disclosure.
Figure 7B:
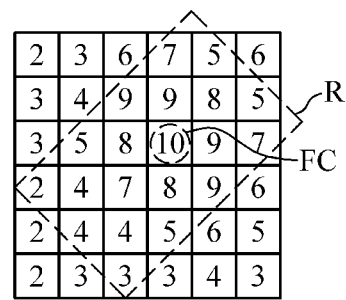

FIG. 5 is a block diagram illustrating an apparatus 500 for analyzing a substance according to yet another embodiment of the disclosure. FIG. 6 is a diagram illustrating an example of a structure of a sensor part of FIG. 5. FIGS. 7A and 7B are diagrams illustrating an example of guiding a contact position based on a fingerprint image.

Referring to FIG. 5, the apparatus 500 for analyzing a substance includes the sensor part 110, the processor 120, an output interface 510, a storage 520, and a communication interface 530. A detailed description of the same elements as those of the apparatuses 100 and 400 for analyzing a substance illustrated in FIGS. 1 and 4 will be omitted, and the following description will be focused on different components.

The sensor part 110 may include a first light source 111, an image sensor 112, and a second light source 113. The first light source 111 may be formed as a plurality of LEDs and the like as described above, and may be disposed around the periphery of the image sensor 112. The image sensor 112 may include a CMOS image sensor. The second light source 113 may be a light source for authentication of a user's fingerprint. The second light source 113 may include one or more LEDs, LDs, and the like.

Referring to FIG. 6, the image sensor 112 may be disposed at the center of the sensor part 110, and the plurality of LEDs 111 may be disposed evenly around the periphery of the image sensor 112. Further, as the second light source 113, one LED may be disposed on one side of the image sensor 112, or two LEDs FL1 and FL2 may be disposed on both sides of the image sensor 112. However, the number and arrangement of the second light source 113 are not limited thereto. Examples of various shapes of the sensor part 110 and various arrangements of the first light source 111 are described in detail above with reference to FIGS. 2A to 2D, such that a detailed description thereof will be omitted.

Once a user places a finger on the sensor part 110, the processor 120 may drive the second light source 113 so that the image sensor 112 may obtain a fingerprint image, and may compare the fingerprint image, obtained by the image sensor 112, with reference fingerprint image data stored in the storage 520, to perform authentication of the user.

For example, if the apparatus 500 for analyzing a substance is mounted in a wearable device or a mobile device such as a smartphone of a specific user, the processor 120 may prevent others from viewing the user's substance analysis data or performing a substance analysis function by using the apparatus 500. Alternatively, the apparatus 500 for analyzing a substance may be mounted in a device, e.g., a large home appliance such as a refrigerator, TV, etc., or devices of medical institutions, which may be shared by a plurality of users. In this case, each of the plurality of users may register a fingerprint image of a finger to be used for authentication of the user in order to use the device. Accordingly, use of the apparatus 500 for analyzing a substance may be controlled by authentication of a user's fingerprint.

The storage 520 may manage data for each of users having authority to use the apparatus 500 for analyzing a substance. For example, the storage 520 may store, for each user, reference fingerprint image data, authority for use of each function, characteristic information, such as a user's age, gender, health condition, etc., which may be used for substance analysis, a light source driving condition, and the like.

Based on successful authentication of a user, the processor 120 may drive the first light source 110 based on a light source driving condition set for the authorized user. Further, upon obtaining a substance analysis result for the authorized user, the processor 120 may update the user's substance analysis history stored in the storage 520.

In addition, based on successful authentication of a user, the processor 120 may guide a contact position of a finger based on a fingerprint image obtained from the user. FIG. 7A illustrates an example of a fingerprint image of a finger. Upon obtaining the fingerprint image, the processor 120 may detect a characteristic point, e.g., a fingerprint center FC and/or a fingerprint direction, from the fingerprint image. In addition, the processor 120 may determine a contact position based on the fingerprint center FC. For example, if a distance between the fingerprint center FC and a center IC of the image sensor 112 is greater than a predetermined threshold value, the processor 120 may determine that a contact position of the finger is not proper.

The output interface 510 may output guide information on the contact position of the finger under the control of the processor 120. For example, the output interface 510 may display the fingerprint image on a display, and may display one or markers, indicating the fingerprint center FC and/or the center IC of the image sensor 112, which are superimposed on the fingerprint image. In addition, if a distance between the fingerprint center FC and the center IC of the image sensor 112 is greater than a predetermined threshold value, the output interface 510 may display a marker (e.g., arrow) for guiding the fingerprint center FC of the finger to move toward the center IC of the image sensor 112.

Further, the processor 120 may determine pixels of a region of interest among pixels of the image sensors 112 based on the fingerprint image, and may obtain absorbance by using light intensities of the determined pixels of the region of interest, as described above. For example, FIG. 7B is a diagram illustrating an example of light intensities of pixels which are received by the image sensor 112. The processor 120 may determine a predetermined region as the region of interest R based on the fingerprint center FC and a contact direction of the finger in the fingerprint image. A size of the region of interest R may be pre-defined. The fingerprint center FC may be determined to be the center of the region of interest R but is not limited thereto. A shape of the region of interest R may be a rectangular shape in the contact direction as illustrated in FIG. 7B, but the shape is not limited thereto, and may be various shapes such as a circular shape, an oval shape, and the like.

In addition, the processor 120 may determine a contact position of the finger based on the fingerprint image, and may determine light sources to be driven among the plurality of light sources 111 based on the determined contact position of the finger. For example, if the fingerprint center FC of the finger is biased in a specific direction, e.g., rightward direction, from the center IC of the image sensor 112, the processor 120 may drive the light sources 111 located on the right side.

The communication interface 530 may receive reference fingerprint image data of a user from, for example, an external device such as a user's smartphone and the like, and may store the data in the storage 520. Alternatively, the communication interface 530 may transmit processing results of the processor 120 to the external device.

Figure 8:
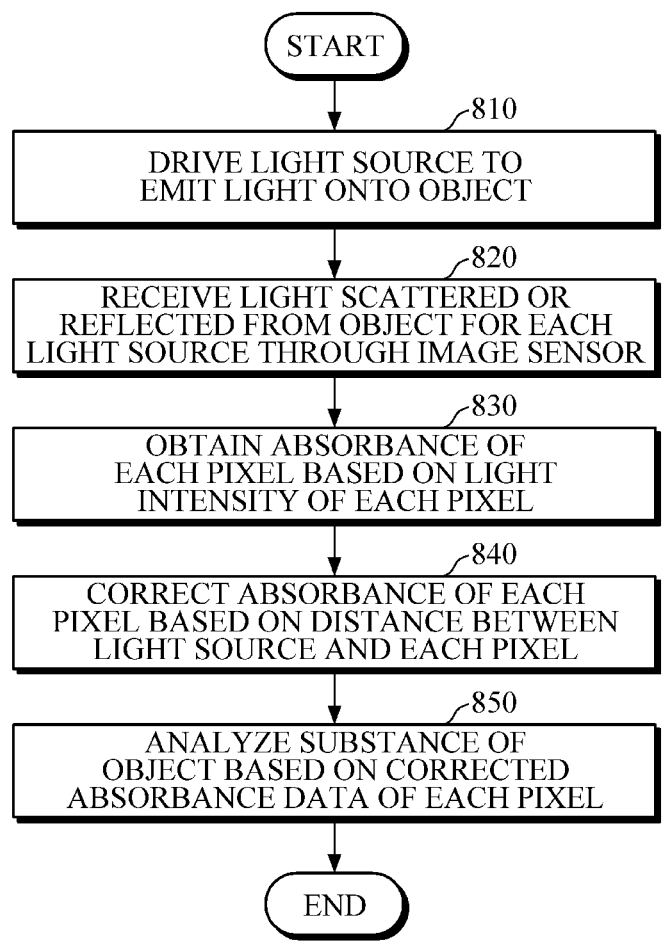
FIG. 8 is a flowchart illustrating a method of analyzing a substance according to an embodiment of the disclosure.

FIG. 8 is a flowchart illustrating a method of analyzing a substance according to an embodiment of the disclosure.

The method of FIG. 8 may be performed by any one of the apparatuses 100 and 400 for analyzing a substance of FIGS. 1 and 4, which are described above in detail and thus will be briefly described below.

The apparatuses 100 and 400 for analyzing a substance may drive a light source to emit light onto an object in 810. A plurality of light sources may be provided, which may emit light of different wavelengths. The apparatuses 100 and 400 for analyzing a substance may combine two or more light sources by considering a measurement position of the object and/or a measurement depth in the object, and may drive the combined light sources. The apparatuses 100 and 400 for analyzing a substance may drive the plurality of light sources in a time-division manner.

Then, the apparatuses 100 and 400 for analyzing a substance may receive light scattered or reflected from the object for each of the driven light sources through an image sensor in 820. In this case, the image sensor may be disposed at the center of a sensor part, and the plurality of light sources may be disposed around the periphery of the image sensor.

Subsequently, the apparatuses 100 and 400 for analyzing a substance may obtain absorbance of each pixel for each of the driven light sources based on light intensities of each pixel which are received by the image sensor in 830.

Next, the apparatuses 100 and 400 for analyzing a substance may correct the absorbance of each pixel of the image sensor based on a distance between the driven light sources and each pixel in 840. For example, the apparatuses 100 and 400 for analyzing a substance may obtain a distance between the driven light sources and each pixel, and may obtain the corrected absorbance of the pixel by dividing an absorbance value of the pixel by the square of the distance. However, a correction equation is not limited thereto, and may be defined in various manners such as a logarithmic function.

Then, upon obtaining the absorbance data of each pixel for the driven light sources, the apparatuses 100 and 400 for analyzing a substance may analyze a substance of the object by using the obtained absorbance data in 850. As described above, based on combination of the absorbance data for each light source, the apparatuses 100 and 400 for analyzing a substance may analyze a substance at each position and depth of the object and at each wavelength.

Figure 9:
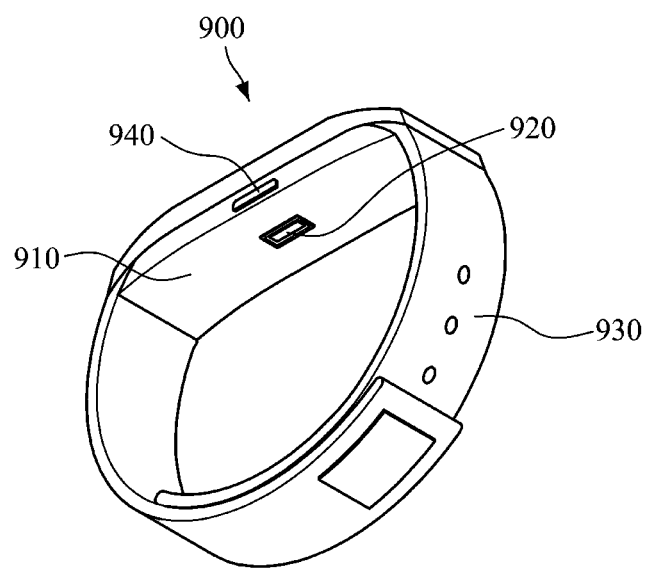
FIG. 9 is a diagram illustrating a wearable device according to an embodiment of the disclosure.

FIG. 9 is a diagram illustrating a wearable device according to an embodiment of the disclosure. The wearable device of FIG. 9 may be a smart watch worn on a wrist or a smart band, and may include one or more of various embodiments of the apparatuses 100, 400 and 500 for analyzing a substance described above.

Referring to FIG. 9, the wearable device 900 includes a main body 910 and a strap 930. Various modules of the apparatus 100, 400 and/or 500 for analyzing a substance may be mounted in the main body 910.

The main body 910 may be worn on a user's wrist using the strap 930. The main body 910 may include various modules for various functions of the wearable device 900. A battery may be embedded in the main body 910 or the strap 930 to supply power to various modules of the wearable device 900. The strap 930 may be connected to the main body 910. The strap 930 may be flexible so as to be bent around a user's wrist. The strap 930 may include a first strap and a second strap which are separated from each other. One ends of the first strap and the second strap are connected to the main body 910, and the other ends thereof may be connected to each other via a connecting means. In this case, the connecting means may include magnetic connection, Velcro connection, pin connection, and the like, but is not limited thereto. Further, the strap 930 is not limited thereto, and may be integrally formed as a non-detachable band.

Furthermore, a sensor part 920 may be mounted in the main body 910. The sensor part 920 may include a CMOS image sensor disposed at the center thereof, and a plurality of light sources disposed around the periphery of the image sensor. The sensor part 920 may have a rectangular shape as illustrated in FIG. 9, or various other shapes, such as a circular shape, an oval shape, etc., according to a shape of a form factor. In this case, the sensor part 920 may include a separate light source for fingerprint authentication.

A processor may be mounted in the main body 910, and may be electrically connected to the modules of the wearable device 900. The processor may obtain absorbance based on light intensities of pixels which are received by the image sensor of the sensor part 920, and may obtain a concentration of an antioxidant, e.g., carotenoid, based on the obtained absorbance. The processor may reduce the effect of distance by correcting the absorbance of each pixel based on a distance between the light sources and each pixel of the image sensor. When a user's finger is in contact with the sensor part 920, the processor may perform user authentication by driving the light source for fingerprint authentication.

Further, the main body 910 may include a storage which stores a variety of reference information, and information processed by various modules.

In addition, the main body 910 may include a manipulator 940 which receives a user's control command and transmits the received control command to the processor. The manipulator 940 may have a power button to input a command to turn on/off the wearable device 900.

Moreover, a display for outputting information to a user may be mounted on a front surface of the main body 910. The display may include a touch screen for receiving touch input. The display may receive a user's touch input and transmit the touch input to the processor, and may display processing results of the processor.

Further, the main body 910 may include a communication interface for communication with an external device. The communication interface may transmit a substance analysis result to the external device, e.g., a user's smartphone.

Figure 10:
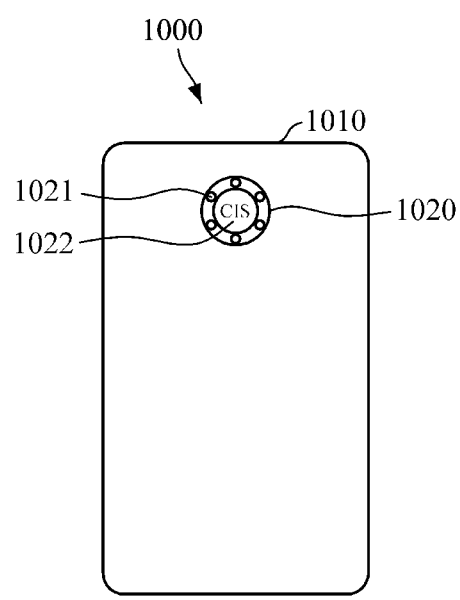
FIG. 10 is a diagram illustrating a smart device according to an embodiment of the disclosure.

FIG. 10 is a diagram illustrating a smart device according to an embodiment of the disclosure. In this case, the smart device may include a smartphone, a tablet PC, and the like. The smart device may include various embodiments of the apparatuses 100, 400 and 500 for analyzing a substance described above.

Referring to FIG. 10, the smart device 1000 includes a main body 1010 and a sensor part 1020 mounted on one surface of the main body 1010. For example, the sensor part 1020 may include a CMOS image sensor 1022 disposed at the center thereof, and a plurality of light sources 1021 disposed around the periphery of the image sensor 1022. In addition, the sensor part 1020 may further include a separate light source for fingerprint authentication. The structure of the sensor part 1020 is described above in detail, such that a description thereof will be omitted.

Moreover, a display may be mounted on a front surface of the main body 1010. The display may visually output a substance analysis result and the like. The display may include a touch screen, and may receive information input through the touch screen and transmit the information to a processor.

The processor may obtain absorbance based on a light intensity of each pixel, which is received by the image sensor when the finger is in contact with the sensor part 1020, and may analyze a substance of an object by correcting the absorbance. In addition, when the finger is in contact with the sensor part 1020, the processor may perform user authentication based on a fingerprint image of the finger. A detailed description thereof will be omitted.

The disclosure may be implemented as a computer-readable code written on a computer-readable recording medium. The computer-readable recording medium may be any type of a recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for implementing the disclosure be readily deduced by programmers of ordinary skill in the art to which the disclosure pertains.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing operations may employ any number of related art techniques for electronics configuration, signal processing and/or control, data processing and the like.

Although a few embodiments have been shown and described, it would be appreciated by those skilled in the art that changes may be made in embodiments without departing from the principles and spirit of the disclosure, the scope of which is defined in the claims and their equivalents.

What is claimed is:

1. An apparatus for analyzing a substance of an object, the apparatus comprising:
   a sensor part including an image sensor and a plurality of light sources, the image sensor comprising a plurality of pixels wherein the image sensor being disposed at the center of the sensor part, the plurality of light sources being disposed evenly around the image sensor, wherein the plurality of light sources are disposed to face each other diagonally with respect to the image sensor;
   the plurality of light sources configured to emit light of a same wavelength, among the plurality of light sources, are disposed to face each other; and
   a processor configured to:
      drive the plurality of light sources to obtain absorbance of each pixel of the image sensor based on an intensity of light received by each pixel;
      correct, for each pixel of the plurality of pixels, the absorbance of each pixel by applying, to the obtained absorbance of each pixel, a value obtained according to a pre-defined function for a distance between the plurality of light sources and each pixel; and
      analyze a substance of an object based on the corrected absorbance of each pixel,
   wherein the processor is further configured to sequentially drive a group of the plurality of light sources, the light sources in the group having different wavelengths and are driven in a time division manner in a predetermined direction centered around the sensor part.

2. The apparatus of claim 1, wherein the image sensor comprises a complementary metal-oxide semiconductor (CMOS) image sensor.

3. The apparatus of claim 1, wherein a first portion of the plurality of light sources are disposed on a first side of the image sensor, and a second portion of the plurality of light sources are disposed on a second side, the second side facing the first side.

4. The apparatus of claim 1, wherein the image sensor comprises a color filter configured to adjust a measurement wavelength band.

5. The apparatus of claim 1, wherein the plurality of light sources are configured to emit light of a single wavelength, and the image sensor comprises a color filter configured to adjust a measurement wavelength band.

6. The apparatus of claim 1, wherein the processor is further configured to, based on at least one of a measurement position or a measurement depth, select light sources among the plurality of light sources to be driven.

7. The apparatus of claim 1, wherein the processor is further configured to combine the corrected absorbance of each pixel for each of the plurality of light sources, and analyze the substance of the object based on a result of combination.

8. The apparatus of claim 1, wherein the processor is further configured to, based on the absorbance of each pixel of the image sensor, analyze the substance for each pixel position of the object.

9. The apparatus of claim 1, wherein the processor is further configured to correct the absorbance of each pixel by applying, to the obtained absorbance of each pixel, a value obtained using a square of the distance between the plurality of light sources and each pixel of the image sensor, or a value obtained using a logarithmic function of the distance between the plurality of light sources and each pixel of the image sensor.

10. The apparatus of claim 1, wherein the processor is further configured to exclude a light source, which does not satisfy a predetermined criterion, based on the absorbance of each pixel with respect to each of the plurality of light sources, and analyze the substance of the object based on the absorbance of each pixel with respect to remaining light sources, excluding the light source.

11. The apparatus of claim 1, wherein the substance of the object comprises at least one of carotenoid, triglyceride, blood glucose, calories, cholesterol, protein, uric acid, or water.

12. An apparatus for analyzing a substance of an object, the apparatus comprising:
a sensor part including an image sensor wherein the image sensor being disposed at the center of the sensor part, a plurality of first light sources disposed evenly around the image sensor, the image sensor comprising a plurality of pixels wherein the plurality of light sources are disposed to face each other diagonally with respect to the image sensor; and a second light source for fingerprint recognition; and
a processor configured to:
drive the second light source to perform user authentication based on a fingerprint image of a finger obtained by the image sensor, and based on a successful user authentication;
drive the plurality of first light sources to obtain absorbance of each pixel of the image sensor based on an intensity of light received by each pixel;
correct, for each pixel of the plurality of pixels, the absorbance of each pixel by applying, to the obtained absorbance of each pixel, a value obtained according to a pre-defined function for a distance between the plurality of first light sources and each pixel; and
analyze a substance of an object based on the corrected absorbance of each pixel,
wherein the processor is further configured to sequentially drive a group of the plurality of light sources, the light sources in the group having different wavelengths and are driven in a time division manner in a predetermined direction centered around the sensor part.

13. The apparatus of claim 12, further comprising a storage configured to store a light source driving condition corresponding to each user,
wherein the processor is further configured to, based on the successful user authentication, drive the plurality of first light sources based on a light source driving condition corresponding to an authenticated user.

14. The apparatus of claim 12, further comprising a storage configured to store a substance analysis history of each user,
wherein the processor is further configured to, based on completion of analysis of the substance of the object, update a substance analysis history of an authenticated user.

15. The apparatus of claim 12, wherein the processor is further configured to provide information related to a contact position of the finger based on the fingerprint image.

16. The apparatus of claim 15, wherein the processor is further configured to detect a position of a characteristic point of the finger based on the fingerprint image, and provide the information based on a distance between the detected characteristic point and a center of the image sensor.

17. The apparatus of claim 12, wherein the processor is further configured to detect a position of a characteristic point of the finger based on the fingerprint image, determine a pixel of interest among pixels of the image sensor, and obtain the absorbance based on an intensity of light at the determined pixel of interest.

18. The apparatus of claim 12, wherein the processor is further configured to detect a position of a characteristic point of the finger based on the fingerprint image, and determine light sources to be driven among the plurality of first light sources based on the detected position of the characteristic point.

19. A method of analyzing a substance of an object, the method comprising:
emitting light onto an object by driving a plurality of light sources disposed evenly around an image sensor, the image sensor being disposed at the center of a sensor part comprising a plurality of pixels;
receiving light, scattered or reflected from the object, through the image sensor;
obtaining absorbance of each pixel of the image sensor based on an intensity of light received by each pixel;
correcting, for each pixel of the plurality of pixels, the absorbance of each pixel by applying, to the obtained absorbance of each pixel, a value obtained according to a pre-defined function for a distance between the plurality of light sources and each pixel; and
analyzing a substance of an object based on the corrected absorbance of each pixel,
wherein in the emitting light, light is emitted under processor control to sequentially drive a group of the plurality of light sources, the light sources in the group having different wavelengths and are driven in a time division manner in a predetermined direction centered around the sensor part.

20. The method of claim 19, wherein the emitting comprises sequentially driving each of the plurality of light sources in a predetermined direction or in a unit of a predetermined wavelength.

21. The method of claim 20, wherein the emitting comprises, based on at least one of a measurement position or a measurement depth, selecting light sources among the plurality of light sources, and sequentially driving the selected light sources in the predetermined direction or in the unit of the predetermined wavelength.

22. The method of claim 19, wherein the analyzing comprises combining the corrected absorbance of each pixel for each of the plurality of light sources, and analyzing the substance of the object based on a result of the combining.

23. The method of claim 19, wherein the analyzing comprises, based on the absorbance of each pixel, analyzing the substance for each pixel position of the object.

24. The method of claim 19, wherein the correcting comprises, correcting the absorbance of each pixel for the plurality of light sources by applying, to the obtained absorbance of each pixel, a value obtained using a square of the distance between the plurality of light sources and each pixel of the image sensor, or a value obtained using a logarithmic function of the distance between the plurality of light sources and each pixel of the image sensor.

25. The apparatus of claim 1, wherein plurality of light sources are disposed evenly around a single CMOS image sensor.

* * * * *